United States Patent [19]

Newton et al.

[11] 4,416,277
[45] Nov. 22, 1983

[54] RETURN ELECTRODE MONITORING SYSTEM FOR USE DURING ELECTROSURGICAL ACTIVATION

[75] Inventors: David W. Newton, Boulder; Frederic M. Hulett, III, Longmont, both of Colo.; Christopher Ovens, San Antonio, Tex.

[73] Assignee: Valleylab, Inc., Boulder, Colo.

[21] Appl. No.: 317,780

[22] Filed: Nov. 3, 1981

[51] Int. Cl.³ .............................................. A61B 17/39
[52] U.S. Cl. ............................... 128/303.13; 128/903
[58] Field of Search ....................... 128/303.13, 303.14, 128/303.17, 134, 90 B

[56] References Cited

U.S. PATENT DOCUMENTS

| 3,683,923 | 8/1972 | Anderson | 128/303.14 |
| 3,933,157 | 1/1976 | Bjurwill et al. | 128/303.14 |
| 3,971,365 | 7/1976 | Smith | 128/734 |
| 4,200,104 | 4/1980 | Harris | 128/303.13 |
| 4,303,073 | 12/1981 | Archibald | 128/303.13 |

FOREIGN PATENT DOCUMENTS 113927 11/1962 Fed. Rep. of Germany ....................... 128/303.17

OTHER PUBLICATIONS

Geddes et al., "The Measurement... Impedance", Am. J. MI, Jan., Mar. 1964, pp. 16-27.

Primary Examiner—Lee S. Cohen
Attorney, Agent, or Firm—Gerald J. Ferguson, Jr.; Joseph J. Baker

[57] ABSTRACT

A return electrode monitoring system for use with a patient return electrode adapted for contacting a patient, the return electrode having two, spaced apart conductors attached thereto for connecting the electrode to a generator of electrosurgical current which passes through the electrode, the system comprising means for applying a monitoring current through the conductors to the electrode; detecting means responsive to the monitoring current for producing a signal which is a function of the impedance between the two conductors, the detecting means including means for substantially eliminating any effect the electrosurgical current might have on the production of the signal when the generator is operational and the patient is in contact with the electrode; means for establishing a desired range having at least an upper limit for the impedance; and determining means responsive to the signal for determining whether the impedance is within the desired range.

17 Claims, 9 Drawing Figures

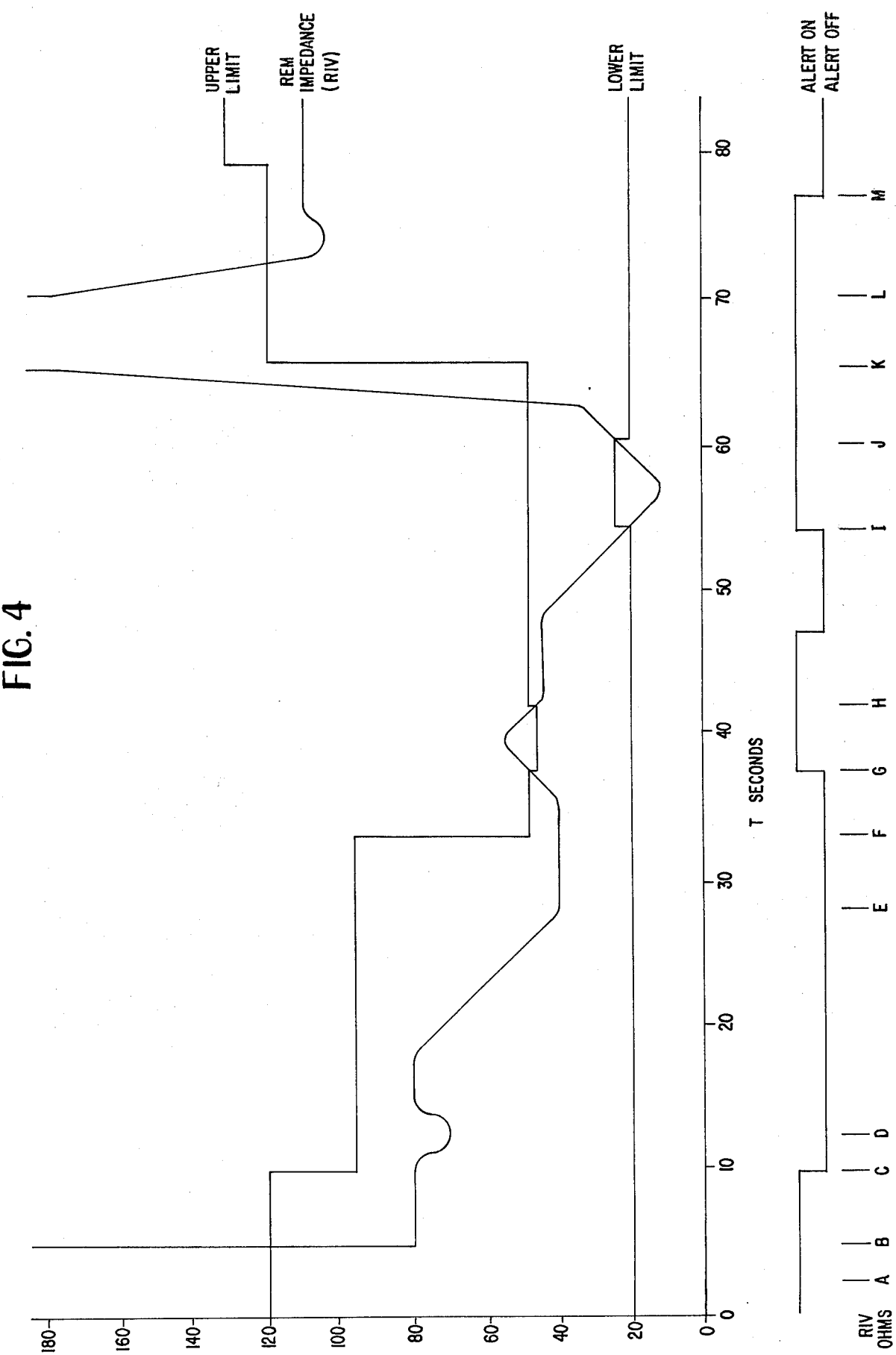

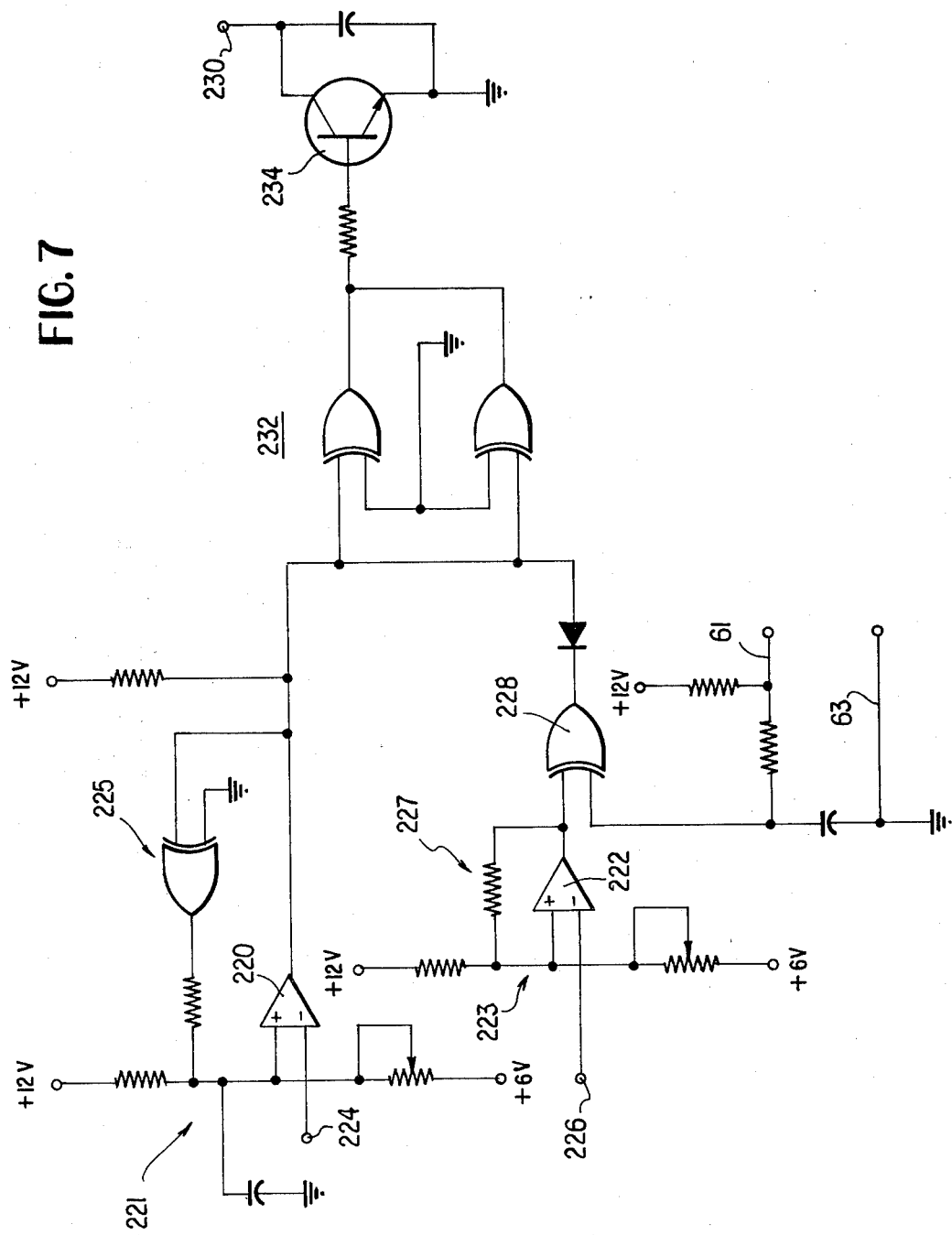

RETURN ELECTRODE MONITORING SYSTEM FOR USE DURING ELECTROSURGICAL ACTIVATION

CROSS REFERENCE TO RELATED APPLICATION

This application is related to an application entitled "Improved Adaptive, Return Electrode Monitoring System" filed in the names of David W. Newton and William G. Paterson on Oct. 26, 1981 and assigned Ser. No. 315,053.

BACKGROUND OF THE INVENTION

This invention is directed to electrosurgery and, in particular, to circuitry for monitoring patient return electrodes employed in such surgery.

One risk involved in electrosurgery is a burn under the patient return electrode. The most common conditions which are thought to lead to such a burn are:

(1) Tenting: Lifting of the return electrode from the patient due to patient movement or improper application. This situation may lead to a burn if the area of electrode-patient contact is significantly reduced.

(2) Incorrect Application Site: Application of a return electrode over a highly resistive body location (i.e. excessive adipose tissue, scar tissue, erythema or lesions, excessive hair) will lead to a greater, more rapid temperature increase. Or, if the electrode is not applied to the patient (i.e. electrode hangs freely or is attached to another surface), the patient is in risk of being burned by contact at an alternate return path such as the table or monitoring electrodes.

(3) Gel drying either due to premature opening of the electrode pouch or to use of an electrode which has exceeded the recommended shelf life.

Many monitor systems have been developed in the past, but most cannot directly guard against all three of the above listed situations. In order to protect against these potential hazard situations, the contact resistance of the return electrode to the patient itself should be monitored in addition to the continuity of the patient return circuit.

Safety circuitry is known whereby split (or double) patient electrodes are employed and a DC current (see German Pat. No. 1,139,927, published Nov. 22, 1962) or an AC current (see U.S. Pat. Nos. 3,933,157 and 4,200,104) is passed between the split electrodes to sense the contact resistance or impedance between the patient and the electrodes. U.S. Pat. No. 3,913,583 discloses circuitry for reducing the current passing through the patient depending upon the area of contact of the patient with a solid, patient plate, there being employed a saturable reactor in the output circuit, the impedance of which varies depending upon the sensed impedance of the contact area.

The above systems are subject to at least one or more of the following shortcomings: (a) lack of sensitivity or adaptiveness to different physiological characteristics of patients and (b) susceptibility to electrosurgical current interference when monitoring is continued during electrosurgical activation.

OBJECTS OF THE INVENTION

Accordingly, it is a primary object of this invention to provide an improved return electrode monitoring system which has little, of ay, susceptibility to electrosurgical current interference when monitoring is continued during electrosurgical activation.

It is further object of this invention to provide an improved return electrode monitoring system where two conductors are connected to a common electrode.

It is a further object of this invention to provide an improved return electrode monitoring system where the type of montoring depends on the type of return electrode employed in the system.

Other objects and advantages of this invention will be apparent from a reading of the following specification and claims taken with the drawing.

BRIEF DESCRIPTION OF THE DRAWINGS

FIG. 4 is a graph illustrating the operation of the adaptive threshold circuitry of FIG. 1.

FIG. 7 is a schematic diagram of circuitry for implementing a non-adaptive function.

DETAILED DESCRIPTION OF PREFERRED EMBODIMENTS OF THE INVENTION

Figure 1:
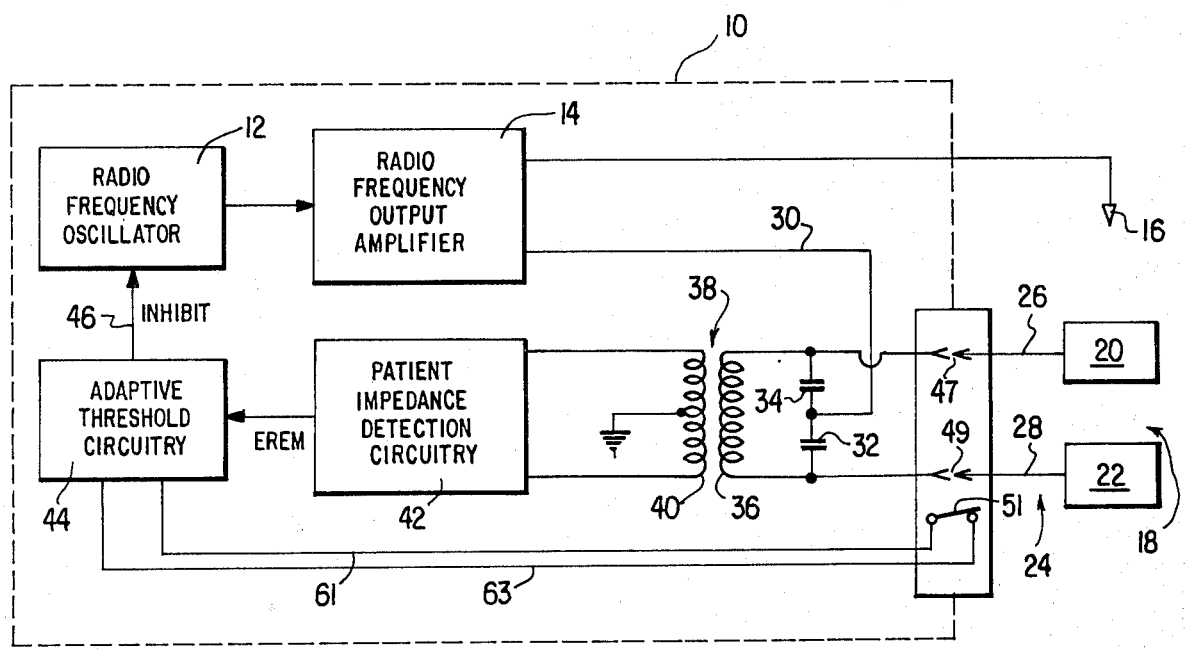
FIG. 1 is a block diagram of an illustrative system in accordance with the invention.

Reference should be made to the drawing where like reference numerals refer to like parts.

Referring to FIG. 1, there is shown a block diagram of the system of the present invention wherein electrosurgical generator 10 may include known circuitry such as a radio frequency oscillator 12 and an output amplifier 14 which generate an electrosurgical current. This current is applied to a patient (not shown) via an active electrode 16. The electrosurgical current is returned to the generator 10 via a split return electrode 18 comrising electrodes 20 and 22 and a two conductor patient cable 24 comprising leads 26 and 28. The split return electrode may be of the type shown in above-mentioned U.S. Pat. No. 4,200,104. The electrosurgical current is then returned to amplfier 14 via a lead 30 connected between capacitors 32 and 34. These capacitors are connected across the secondary winding 36 of a transformer 38.

The primary winding 40 of the transformer is connected to patient impedance detecting circuitry 42, the purpose of which is to produce a voltage EREM which is a function of the impedance between electrodes 20 and 22. EREM is applied to adaptive threshold circuitry 44 which determines whether the above impedance is within a desired range, the range being preferably adaptable to the physiological characteristics of the patient. If it is not, an inhibit signal is applied over a line 46 to internally disable the generator.

A plug attached to the generator end of two conductor cable 24 is insertable into a patient connector which is incorporated in generator 10. The plug/connector arrangement is diagrammatically indicated at 47 and 49.

A switch 51 in the connector is also provided to indicate the mode of operation of the system. That is, in a first mode, the system employs the split patient electrode 18 of FIG. 1. Incorporated in the plug for the split patient return electrode cable is a pin which activates switch 51 to thereby indicate over lines 61 and 63 to adaptive threshold circuitry 44 the system is operating in its first mode—that is, with a split patient electrode.

Figure 1A:
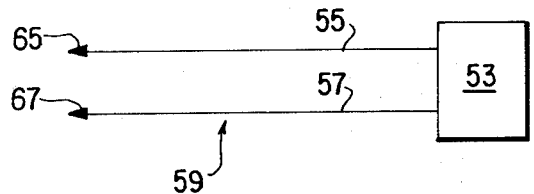
FIG. 1A is a diagrammatic illustration of a common foil electrode and associated cable for use in the system of FIG. 1.

Diagrammatically illustrated in FIG. 1A is an electrode arrangement employed in a second mode of operation of the system, the electrode 53 comprising a common foil having connected thereto at spaced apart points the leads 55 and 57 of a two conductor cable 59. A plug attached to the generator end of the cable is insertable in the connector disposed at the generator. However, it does not include a pin corresponding to that described above. Hence, when the plug of the FIG. 1A arrangement is inserted in the connector, switch 51 is not activated. Accordingly, an indication is provided over lines 61 and 63 the system is cooperating in its second mode of operation.

Figure 2:
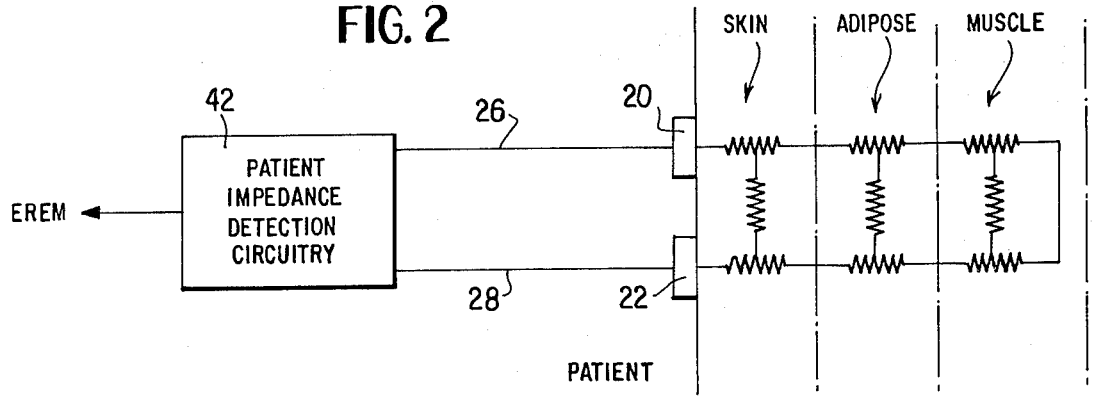
FIG. 2 is a diagrammatic illustration indicating physiological characteristics affecting the impedance between the elements of a split patient electrode when the electrode is in contact with a patient's skin.

In FIG. 2, patient impedance detection circuitry 42 is shown connected to electrodes 20 and 22 which in turn are in contact with the patient's skin. Further, the physiological characteristics of the patient's skin, adipose and muscle layers are diagrmmatically indicated by resistances. As will be described in detail hereinafter, detection circuitry 42 applies a constant, physiologically benign, monitor current (typially 140 kHz, 2 mA) to conductor 26 which passes through electrode 20 and the patient and then returns to ciruitry 42 via electrode 22 and conductor 28. Circuitry 42 processes the voltage appearing across conductors 26 and 28 to provide EREM which, as stated above, is a measurement of the impedance between electrodes 20 and 22.

Adaptive threshold circuitry 44 typically establishes a range, which may extend from 20 to 144 ohms, within which the impedance between the electrodes (pads) 20 and 22 must fall. If not, the generator 10 is disabled. Thus, the lower limit is fixed at the nominal value of 20 ohms whereby such hazards as applying the electrode to a surface other than the patient may be avoided. The upper limit is set to avoid such problems as those mentioned hereinbefore—that is, tenting, incorrect application site, gel drying, etc.

In accordance with an important aspect of the invention, the upper limit is adjustable from the absolute maximum (typically 144 ohms) downward to as low as typically 20 ohms to thereby provide for automatic adaptiveness to the physiological characteristics of the patient. This provides the monitor of the present invention with significantly more control over the integrity of the return electrode connection without limiting the range of patient types with which the system may be used or burdening the operator with additional concerns. That is, the physiological characteristics indicated in FIG. 2 can very significantly from patient to patient and from one location site for the return electrode to another. Thus, patients, of course, vary in their respective amounts of adipose tissue. Further, for a particular patient, one location site may be more fatty, hairy or scarred than another. All of the factors may affect the impedance measured between electrodes 20 and 22 and thus concern the operator as to which site is optimal for a particular patient. As stated above, such concerns are eliminated in the present invention by providing for automatic adaptability to the physiological characteristics of the patient.

Figure 3:
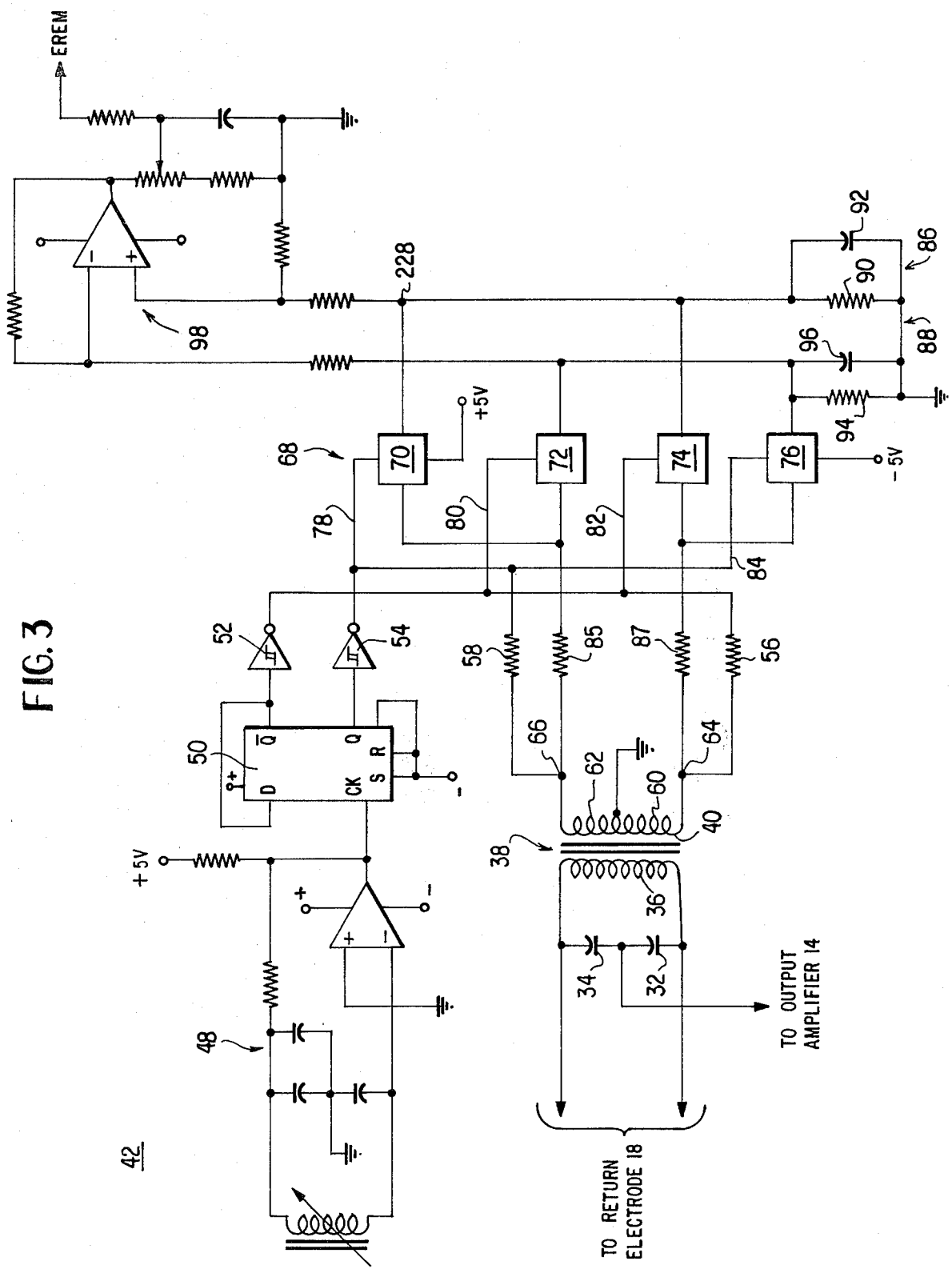
FIG. 3 is a schematic diagram of the patient impedance detection circuitry of FIG. 1.

Referring now to FIG. 3, there is shown a circuit digram of patient impedance detection circuitry, which comprises an oscillator indicated at 48. The output of the oscillator is connected to a flip-flop 50 which provides a symmetrical square wave of typically 140 kHz. The outputs of flip-flop 50 are applied to 52 and 54 which provide fast edges for accurate multiplexer operation, as described below.

Constant currents from 52 and 54 pass through resistors 56 and 58 and thence through the respective halves 60 and 62 of primary winding 40 of transformere 38. The impedance reflected to the primary side of the transformer will vary as a function of the impedance between electrodes 20 and 22. Accordingly, in view of the constant currents flowing through resistors 56 and 58 the voltages appearing at terminals 64 and 66 will vary as the above impedance. It is these voltages which are processed to derive EREM.

A synchronous detector 68 comprising analog transmission gates 70-76 rejects electrosurgical current which may appear at terminals 64 and 66. Thus, in accordance with another important aspect of the invention, monitoring of the return electrode circuit may not only be effected prior to electrosurgical activation but may also be continued during such activation. Since the 140 kHz gating signals applied over lines 78-84 to gates 70-76 are in phase with the 140 kHz sense currents flowing into terminals 64 and 66 from resistors 56 and 58, the sensing signals applied to the gates from these terminals via resistors 85 and 87 will be passed by the gates and additively applied to RC circuits 86 and 88 where RC circuit 86 comprises resistor 90 and capacitor 92 and RC circuit 88 comprises resistor 94 and capacitor 96. However, the 750 kHz electrosurgical current signal will be orthoganal to the 140 kHz gating signal and thus, over a period of time the electrosurgical signals applied to RC circuits 86 and 88 will substract from one another to thereby provide a very high degree of rejection of the electrosurgical current signal and any other noise. The signals appearing across RC circuits 86 and 88 are applied to a differential amplifier circuit 98, the output of the circuit being EREM.

Reference should now be made to FIG. 4 which is a graph illustrating the operation of adaptive threshold circuitry 44.

The return electrode monitor (REM hereinafter) impedance range (that is, the acceptable range of the impedance detected between electrodes 20 and 22) is preset when the power is turned on to an upper limit of 120 ohms and a lower limit of 20 ohms as can be seen at time T=0 seconds in FIG. 4. If the monitored impedance is outside of this range (T=A seconds) for example, when the return electrode is not affixed to the patient, an REM alert will be asserted and the generator will be disabled over line 46. The REM impedance at any instant is designated the REM Instantaneous Value (RIV) in FIG. 4. When the REM impedance enters the range (T=B seconds) bounded by the Upper Limit (UL), the Lower Limit (LL), a timing sequence begins. If after five seconds the RIV is still within range (T=C seconds), the alert condition will cease and the REM impedance value is stored in memory. This is designated as REM Nominal Value (RNV). The upper limit is then reestablished as 120% of this amount. The 80 ohm RIV shown in FIG. 4 causes the upper limit to be at 96 ohms. This feature of the invention is particularly important because it is at this time (T=C seconds) that adaptation is initially made to the physiological characteristics of the patient. Note if the RIV were to exceed 96 ohms at a time between T=C and T=F second (while the upper limit is 96 ohms), the alert will be asserted and the generator disabled. However, if the upper limit had not been adjusted to 96 ohms, the alert would not have been asserted until after the RIV exceeded the initial 120 ohms upper limit, thus possibly subjecting the patient to undue heating at the split return electrode. This situation is of course exacerbated if the patient's initial RIV within the preset 20 to 120 ohm range is 30 ohms, for example.

An initial RIV of 10 ohms within the preset range of 20 to 120 ohms sets an upper limit of 144 ohms.

In accordance with another aspect of the invention, it has been observed the REM impedance decreases over a relatively long period such as a number of hours. Since many surgical procedures can extend a number of hours, this effect is also taken into consideration in the present invention. Accordingly, RIV is continuously monitored and any minima in REM impedance, i.e. a downward trend followed by a constant or upward trend in REM impedance, initiates a new five second timing interval (T=E seconds) at the end of which the RNV is updated to the RIV if the RIV is lower (T=F seconds). The REM upper limit of 120% of RNV is re-established at this time. The five second interval causes any temporary negative chage in REM impedance (T=D seconds) to be disregarded. Operation will continue in this manner providing RIV does not exceed the upper limit of 120% RNV or drop below the lower limit of 20 ohms. Exceeding the upper limit (T=G seconds) causes a REM alert and the generator is disabled. It will remain in alert until the RIV drops to 115% of RNV or less (T=H seconds) or until the REM system is reinitialized. RIV dropping to less than 20 ohms (T=I seconds) causes a similar alert which continues until either the RIV exceeds 24 ohms (T=J seconds) or the system is reinitialized. The hysteresis in the limits of the REM range (that is, the changing of the upper limit to 115% of RNV and the lower limit to 24% ohms in the previus examples) prevents erratic alerting when RIV is marginal.

It should be noted in the example of FIG. 4 the alert actually does not turn off when RIV returns to a value greater than 24 ohms because the split return electrode is removed before 5 seconds after T=J seconds elapse. Thus, the alarm stays on due to the removal of he electrodes.

Removing the return electrode from the patient or unplugging the cable 24 from generator 10 (T=K seconds) for more than one second causes the REM system to be reinitialized to the original limits of 120 and 20 ohms. This permits a pad to be relocated or replaced (T=L seconds) without switching the generator off. The RIV at the new location is 110 ohms and 120% RNV is 132 ohms. Thus, as described above, this is the one time (whenever RIV enters the 20 to 120 ohms range (either as preset during power on or as reinitialized as at T=K seconds) for the first time) that the upper limit can be raised during the normal REM cycle. Otherwise, it is continually decreased to adapt to the decreasing RIV impedance with the passage of time.

The preferred implementation of the foregoing FIG. 4 operation of the adaptive threshold circuitry 44 is effected by a programmed mircoprocessor such as the INTEL 8048. Attached hereto as an Appendix is a program for the INTEL 8048 for implementing the FIG. 4 operation.

Figure 5A:
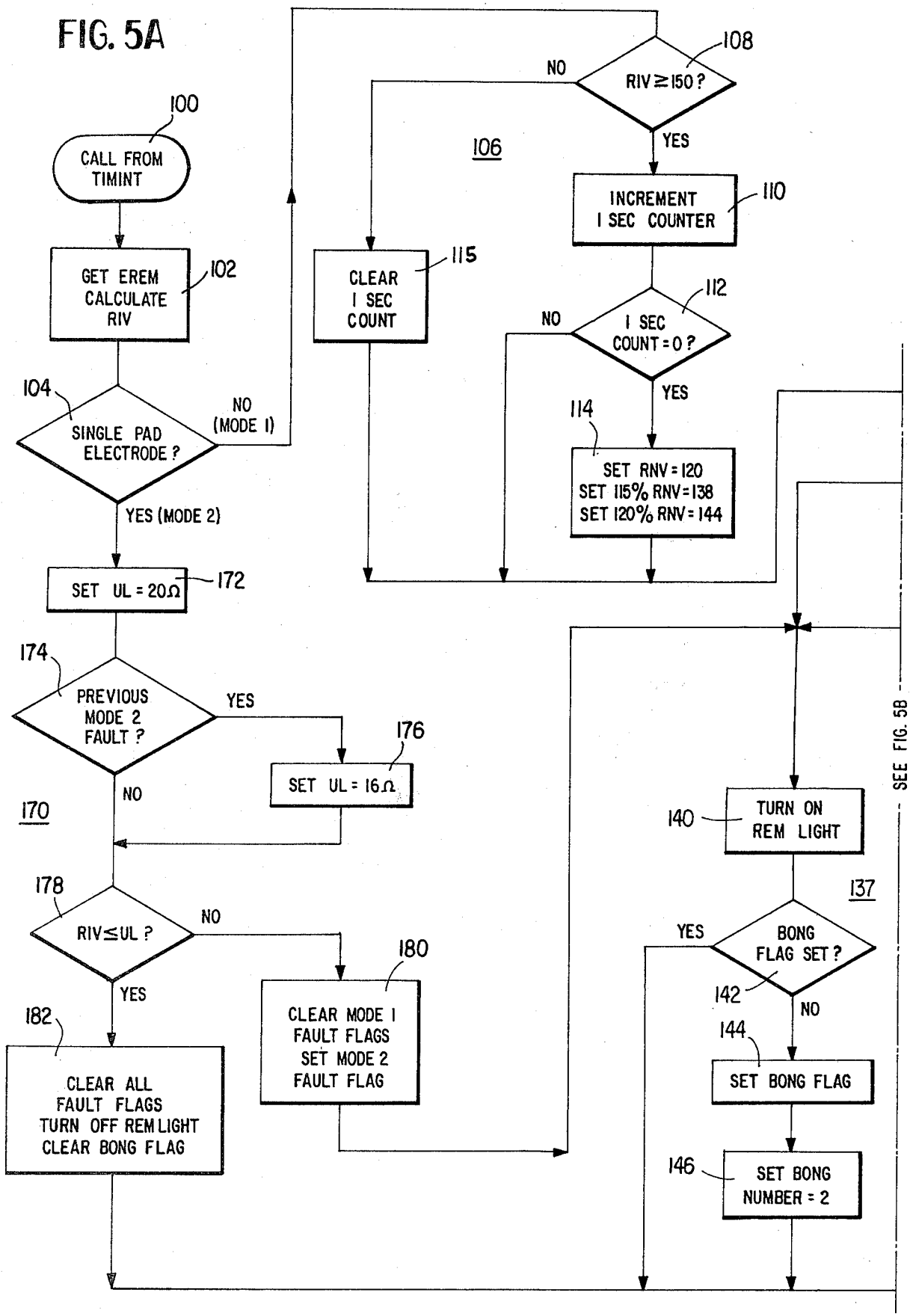
FIGS. 5A and 5B are a flow chart of a program for implementing the operation illustrated by FIG. 4.
Figure 5B:
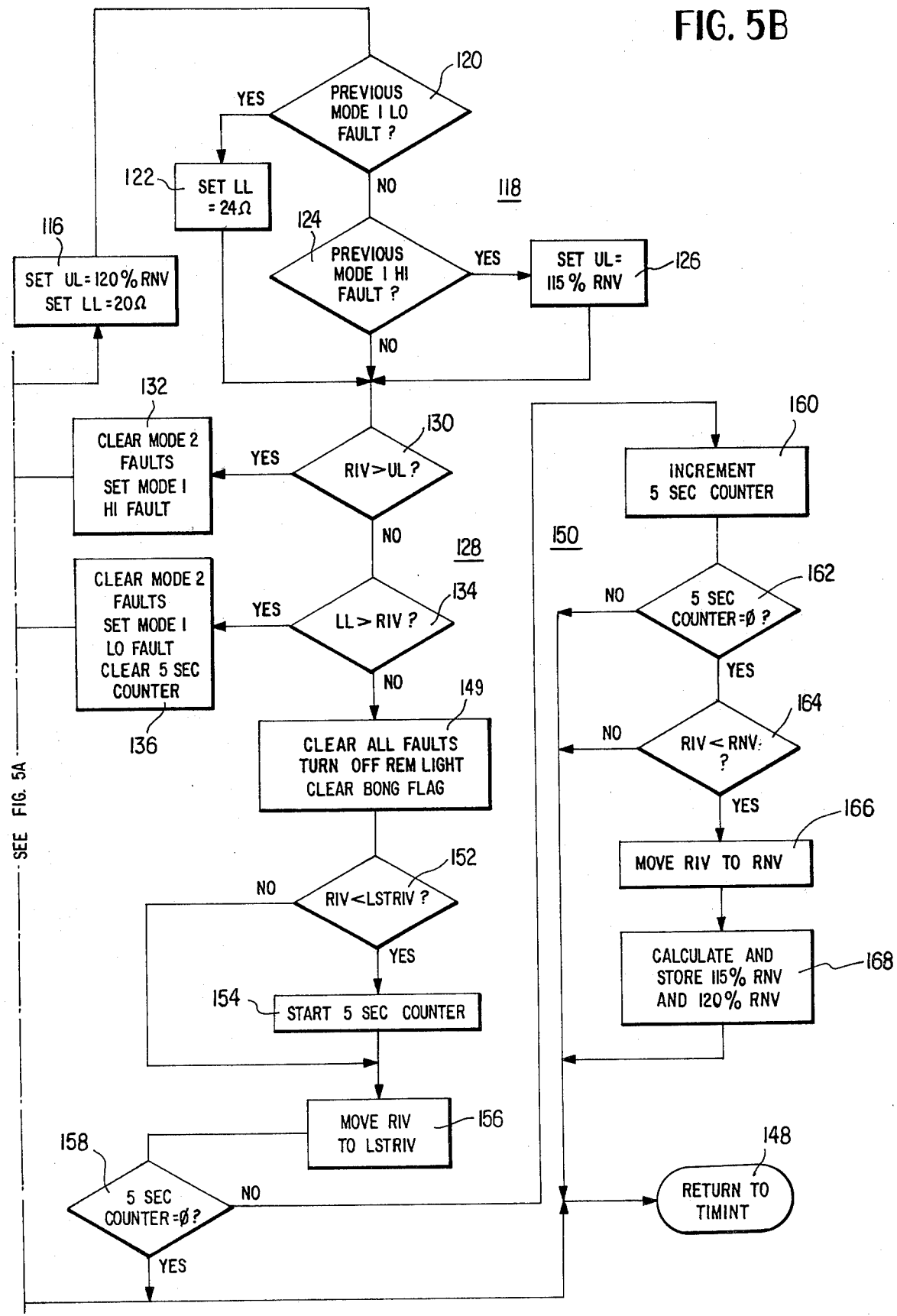

Reference should now be made to FIGS. 5A and 5B, which are a flow chart of the above-mentioned program. As indicated at 100, the program is called by another program TIMINT (Timing Interrupt) which samples EREM approximately 50 times every second. First, RIV is calculated at portions 102 of the program in accordance with the following equation:

$$RIV = [EREM/(I_{sense} - I_{shunt})] \qquad (1)$$

where $I_{sense}$ is the constant current flowing through resistors 56 and 58 of Figure and $I_{shunt}$ is shunt current which flows through shunt paths in transformer 38 and through resistors 85 and 87. Ideally $I_{shunt}$ would not be present and EREM would only be a function of the variable RIV and the constant current $I_{sense}$. However, not all of $I_{sense}$ is employed to produce EREM because of the above-mentioned shunt paths. $I_{shunt}$ may be determined from the parameters of the circuit of FIG. 3 and thus RIV is readily calculated in accordance with equation (1).

A determination is next made at step 104 as to which mode of operation the system is in. Assuming switch 51 has been activated, the system is in its first mode of operation and a split return electrode is bein used. The program now moves to a portion generally indicated at 106 comprising steps 108-116, the purpose of which is to implement the function described at T=K seconds of FIG. 4 whereby removal of electrode 18 or unplugging of cable 24 for more than approximately one second causes reinitialization of the system. That is, as indicated as step 114, RNV is reset to 120 ohms, 115% RNV to 138 and 120% RNV to 144 ohms where RNV, 115% RNV and 120% RNV are preset to these values at the time power is initially applied to the generator. Another parameter LSTRIV (LAST RIV), which will be discussed below, is also preset to 120 ohms at the time of initial power application. At step 108, a determination is made as to whether RIV is greater than 150 ohms (that is, whether electrode 18 has been removed or cable 24 unplugged). If so, a one second counter is incremented at step 110. Fifty increments (corresponding to the 50 samples per second of EREM) will cause the counter to overflow to zero at one second. Thus, if the counter is set to zero, this indicates one second has elapsed since electode 18 was removed or cable 24 was uplugged whereby the program will pass from step 112 to step 114 to effect the resetting of RNV, 115% RNV and 120% RNV as described above. If RIV is less than 150 ohms, the one second counter is cleared at step 115.

The program passes from portion 106 to step 116 where the upper limit UL is set to 120% RNV and the lower limit LL is set to 20 ohms.

The program next moves to portion 118 which includes steps 120-126. This portion provides the hysteresis in the limits of the REM range illustrated at T=G or I of FIG. 4. Thus, as will be described below, when RIV drops below 20 ohms, a mode one lo (low) fault flag will be set. When EREM is sampled again approximately 1/50 second later, the mode one lo fault flag will still be set as detected at step 120 and the lower limit LL will be reset to 24 ohms at step 122 as illustrated at T=I. In a similar manner, the upper limit UL will be reset to 115% RNV at steps 124 and 126 as illustrated at T=G assuming a previous mode one hi (high) fault has occurred.

The program now passes to portion 128 which includes steps 130-136 where the actual determinations are made as to whether RIV has remained with the desired range extending between UL and LL. If RIV is greater than UL(T=G), this is determined at step 130 and indicates the presence of a fault. Accordingly, at step 132, any previous mode two fault (to be described hereinafter) is cleared and the mode one hi fault flag is set.

Appropriate alarms may then be activated at portion 137 of the program and the INHIBIT signal on line 46 of FIG. 1 is generated to disable the generator. Rather than generating the INHIBIT signal directly from the FIG. 6 program, it may also be done (and is done in the actual implementation of the invention) by communicating REM status information (such as the status of the mode one hi and lo faults) to a main program (which effects other operations associated with the generator 10 not forming a part of this invention) via specific registers. These registers are continually checked and if any REM fault bits are set, the generator is disabled.

Portion 137 includes steps 140–146. Step 140 turns on an REM alarm light. A sound alarm may also be activated to provide a predetermined number of bongs. If this alarm has not been activated, this will be determined at step 142 whereby at step 144, a bong flag will be set to indicate actuation of the sound alarm. The number of bongs produced by the alarm is determined at step 146 where, in this example, the number is two. Even though the generator has been disabled and alerts have been turned on, the system will continue to monitor RIV.

In a manner similar to that described above, a test is made at step 134 to determine if the lower limit LL is greater than RIV. If it is, any previous mode two fault is cleared, the mode one lo fault flag is set and a five second counter, which will be discussed below, is also cleared.

Assuming RIV is within the range established by the current value of UL and LL, the program passes to stop 149 where any previous fault (which may have been set at steps 132 136 or 180) is cleared, REM alert lights (which may have been turned on at step 140) are turned off and the bong flag (whichmay have been set at step 144) is cleared.

The program then moves to portion 150 which includes steps 152–168. At portion 150, a determination is made as to whether any new minimum in RIV, resulting either from RIV entering the desired range for the first time as at T=B or L or from a decrease in value thereof as at T=D or E, should be disregarded as being a transient. If the minimum lasts more than five seconds, it is not disregarded and RNV is updated to the RIV if RIV is lower as indicated at T=F. Thus, at step 152, a determination is made as to whether the current RIV is less than the last RIV (LSTRIV). If it is not (that is equal to or greater than) the current RIV is immediately moved at step 156 to a register for storing LSTRIV and thus becomes the last RIV for the next sample of EREM. If RIV is increasing in such a manner that it is moving out of the desired range, this will quickly be detected at step 130 as successive samples of EREM are processed, at which time, portion 136 will be activated to disable the generator and turn on appropriate alarms.

If RIV is less than LSTRIV, this indicates the possible occurrence of a non-transient minimum and thus, a five second counter is started at step 154. The operation of this counter is similar to the one second counter previously discussed and after 250 successive increments thereof, approximately five seconds will have elapsed which is indicated by the counter overflowing to zero. After starting the counter, the new lower RIV is moved to LSTRIV at step 156. Of course, if RIV ever becomes less than 20 ohms, this will be detected at step 134.

A check is next made at step 158 as to whether the five second counter has been started. If it has, the program returns to TIMINT preparatory to processing the next sample. If it hasn't, the five second counter is incremeneted at step 160 and again, at step 162, a check is made to see if five seconds have elapsed on the counter. If not, the program returns to TIMINT. If it has, a check is made at step 164 to see if RIV is less than RNV. If RIV is not less than RNV, this indicates the downward trend initially detected in RIV was transient and is thus disregarded and the program returns to TIMINT. However, if RIV is less than RNV, a non-transient minimum has occurred whereby the current RIV becomes the new RNV as indicated at step 166. The new values of 115% RNV and 120% RNV are also calculated and stored at step 168.

As stated above, the system is placed in its second mode of operation, when single foil electrode 53 of FIG. 1A is employed. Portion 170 of the program is used to assure continuity of the cable/electrode of FIG. 1A and its connection to the generator. Only an upper resistance limit of typically 20 ohms is employed. The above continuity is verified when the measure resistance between the two connector prongs is less than 20 ohms. A resistance of greater than 20 ohms causes a REM alert, and the generator is inhibited over line 46. Causing the resistance to decrease to less than 16 ohms, typically by replacing the cord/return electrode, will clear the REM fault condition.

Accordingly, portion 170 of the program includes steps 172–182 whereby if, at step 104, it is determined the system is in its second mode of operation, the upper limit is set to 20 ohms at step 172. If there has been a previous mode two fault, the upper limit is decreased to 16 ohms at step 176 in a manner similar to the decrease that occurs in the mode one upper limit at step 126. A check is then made at step 178 to determine whether RIV is less than or equal to the upper limit. If it is not, a fault has occurred. Thus, at step 180, any previous mode one fault flags are cleared and the mode two fault flag is set. The program then enters portion 137 at which time the generator is disabled and appropriate alerts are turned on, as described above. If RIV is less than or equal to UL, all fault flags are cleared, the REM alert light is turned off and the bong flag is cleared prior to returning to TIMINT.

Figure 6:
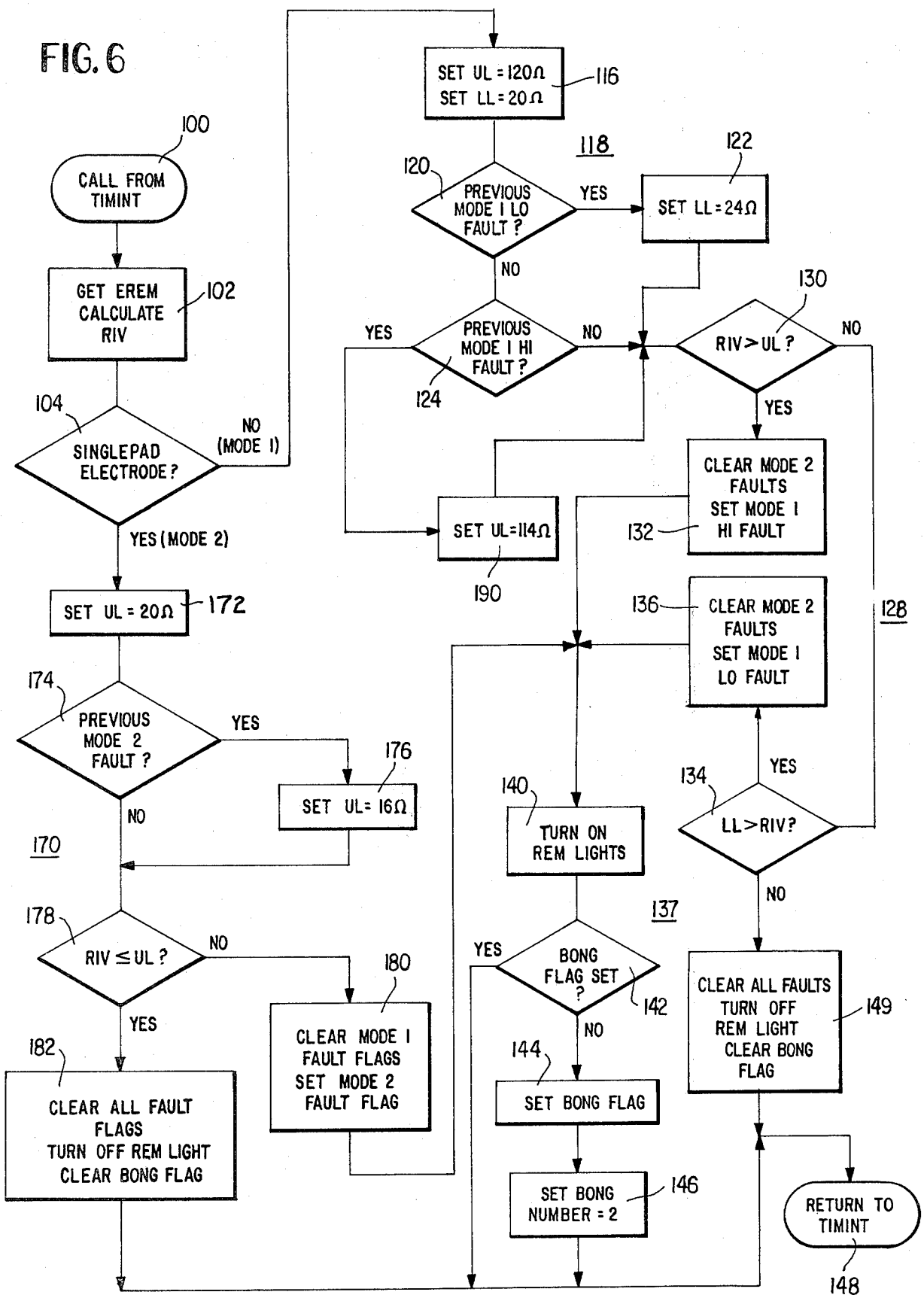
FIG. 6 is a flow chart of a program for implementing a non-adaptive threshold function.

Reference should now be made to FIG. 6 which is a flow chart of a computer program which may be used in a non-adaptive system. In a non-adaptive system, the upper and lower limits are fixed typically at 120 and 20 ohms. Of course, the advantages of the adaptive system as described hereinbefore are not available. However, the protection afforded by such a system is adequate in many applications.

As can be seen in FIG. 6, the program for a non-adaptive system is a simplified version of the FIG. 5 adaptive program. Hence, in FIG. 6, there is no portion 106 to reinitialize the upper limit since the upper limit is not changed. The same applies to portion 150 of the FIG. 5 program where the upper limit is downwardly adjusted with the passage of time. Accordingly, portions 106 and 150 are not included in the non-adaptive program of FIG. 6. The remaining portions of the FIG. 6 program are the same as the corresponding portions of the FIG.

5 program with the following exceptions. In portion 118, the upper limit is set to 114 ohms if there has been a previous mode one hi fault at step 190. Further, there is no need to clear a five second counter as is done at step 136 of the FIG. 5 program. With these exceptions, the operation of the FIG. 6 program corresponds to that described above for the FIG. 5 program. Hence, the operation of the FIG. 6 program will not be repeated here.

The software embodiment of FIG. 6 is preferred for implementing a non-adaptive system when a processor such as the INTEL 8048 is employed for effecting other functions of the generator. However, when such a processor is not employed, a preferred implementation would be the threshold circuitry shown in FIG. 7. This circuitry includes comparators 220 and 222 which are respectively set via voltage dividers 221 and 223 to provide the high and low limits of 120 and 20 ohms. Input terminals 223 and 226 preferably are connected to output terminal 228 of the synchronous detector 68. Thus, a double-ended output is presented so that the detector will be symmetrically loaded; however, only the output occurring at terminal 228 is used by the comparator circuits. If they are connected to terminal 228, the operational amplifier circuitry 98 of FIG. 3 may be eliminated. Alternatively, the EREM output of FIG. 3 may be applied to terminals 224 and 226 of FIG. 7. Hysteresis is respectively provided via elements 225 and 227 on comparators 220 and 222 to provide stable switching.

Exclusive OR gate 228 is keyed by the signal occurring on lines 61 and 63 of FIG. 1 to thereby establish the mode of operation of the threshold circuitry. Thus, if a common foil electrode is employed (mode two), the low resistance value of comparator 222 is employed as the upper limit. If the input signal at terminal 226 exceeds this upper limit signal established at the other input to comparator 222, an inhibit is applied to terminal 230 (connected to line 46 of FIG. 1) via gates 228 and 232 and inverter 234 to thereby disable the generator.

If a split patient electrode is employed (mode one), the low resistance value of comparator 222 is employed as the lower limit and the high resistance value of comparator 220 is employed as the upper limit. If either the input signal at terminal 224 exceeds the upper limit established at comparator 220 or the input signal at terminal 226 is less than the lower limit established at comparator 222, an inhibit signal is applied to terminal 230. Appropriate visual and sound alarms may also be provided as needed upon occurrence of the inhibit signal.

It is to be understood that the above detailed description of the various embodiments of the invention is provided by way of example only. Various details of design and construction may be modified without departing from the true spirit and scope of the invention as set forth in the appended claims.

We claim:

1. A return electrode monitoring system for use with a patient return electrode adapted for contacting a patient, said return electrode having two, spaced apart conductors attached thereto for connecting the electrode to a generator of electrosurgical current which passes through the electrode, said system comprising means for applying a monitoring current through said conductors to said electrode;

detecting means responsive to said monitoring current for producing a signal which is a function of the impedance between said two conductors, said detecting means including means including a synchronous detector for substantially eliminating any effect the electrosurgical current might have on the production of said signal when said electrosurgical and monitoring currents are simultaneously applied to said return electrode;

means for establishing a desired range having at least an upper limit for said impedance; and determining means responsive to said signal for determining whether said impedance is within said desired range whereby said monitoring system is susceptible to negligible interference from the electrosurgical current when monitoring is continued during application of the electrosurgical current to the patient.

2. A system as in claim 1 wherein said means for establishing a desired range includes means for generating a reference signal corresponding to the upper limit and where said determining means includes comparator means for comparing the signal which is a function of said impedance with the reference signal.

3. A system as in claim 1 where said desired range includes a lower limit for said impedance and where said means for establishing a desired range includes means for generating a reference signal corresponding to the lower limit and where said determining means includes comparator means for comparing the signal which is a function of said impedance with the reference signal.

4. A system as in claim 1 where said means for applying the monitoring current includes an oscillator which also generates a gating signal for the synchronous detector.

5. A system as in claim 4 where said means for applying the monitoring current also includes a transformer for coupling the two conductors to the oscillator, the secondary winding of the transformer being connected to the two conductors and the primary winding thereof being in circuit with the output of the oscillator where the output of the oscillator is a constant current so that the impedance reflected from a secondary circuit including the electrode and the two conductors to the primary winding causes the voltage across the primary winding to follow any variations in the impedance between said two conductors.

6. A system as in claim 5 where said synchronous detector is connected across said primary winding.

7. A system as in claim 1 where the frequency of said electrosurgical current is substantially different from that of said monitoring current.

8. A system as in claim 7 where the frequency of the electrosurgical current is 750 kHz and that of the monitoring current is 140 kHz.

9. A system as in claim 1 where said return electrode is single foil electrode with the two conductors attached at spaced apart points on the electrode.

10. A system as in claim 1 where said return electrode is a split patient electrode having two, electrically isolated electrode elements with the two conductors respectively attached to the elements.

11. A return electrode monitoring system for use with a return electrode adapted for contacting to a patient, said return electrode being either (a) a split patient electrode having two, electrically isolated electrode elements with two conductors respectively attached to the elements and a first plug attached to said two conductors for connecting the split patient electrode to a generator of electrosurgical current where said first plug includes switch actuating means, or (b) a single foil electrode with two conductors attached at spaced apart points on the single foil electrode and a second plug attached to the latter two conductors for connecting the single foil electrode to the generator, said system comprising electrode detecting means for detecting whether the return electrode is of the split patient type or the single foil type, said electrode detecting means including a switch responsive to said switch actuating means in the first plug to detect the presence of said split patient type return electrode and being non-responsive to said second plug to detect the presence of said single foil type return electrode;

means responsive to the impedance between the two conductors for producing a signal which is a function of said impedance regardless of which type of return electrode is employed;

means for establishing a first desired range having an upper and a lower limit for said impedance when (a) the split patient electrode is employed and (b) the patient is in contact with the electrode elements;

means for establishing a second desired range having at least an upper limit for said impedance when the single foil electrode is employed;

first determining means responsive to said electrode detecting means detecting the employment of a split patient electrode for determining whether said impedance is within said first desired range; and second determining means responsive to said electrode detecting means detecting the employment of a single foil electrode for determining whether said impedance is within said second desired range.

12. A system as in claim 11 where said lower limit of the first desired range equals the upper limit of the second desired range.

13. A return electrode monitoring system for use with a single foil, patient return electrode adapted for contacting a patient, said electrode having two, spaced apart conductors attached thereto for connecting the electrode to a generator of electrosurgical current, said system comprising means responsive to the impedance between said two conductors for producing a signal which is a function of said impedance;

means for establishing a desired upper limit for said impedance;

determining means responsive to said signal for determining whether said impedance is below said desired upper limit; and transition detecting means for detecting a transition of said impedance from a value less than said upper limit to a value greater than said upper limit and means for decreasing the value of the upper limit to a lower value in response to said transition.

14. A system as in claim 13 where said means for establishing a desired upper limit includes means for generating a reference signal corresponding to the upper limit and where said determining means includes a comparator means for comparing the signal which is a function of said impedance with the reference signal.

15. A return electrode as in claim 13 where said desired upper limit is 20 ohms.

16. A system as in claim 13 including means for disabling the system in response to the occurrence of the transition.

17. A system as in claim 13 including means for generating an alarm signal in response to the occurrence of the transition.

* * * * *